United States Patent [19]

Egan et al.

[11] 4,098,822

[45] Jul. 4, 1978

[54] MIXTURES OF ALIPHATIC AMINES AND QUATERNARY AMMONIUM COMPOUNDS THEREOF

[75] Inventors: Richard R. Egan, Worthington, Ohio; Graham K. Hughes, Hackettstown, N.J.; Jack W. Sigan, Minneapolis, Minn.

[73] Assignee: Ashland Oil, Inc., Ashland, Ky.

[21] Appl. No.: 409,965

[22] Filed: Oct. 26, 1973

Related U.S. Application Data

[60] Division of Ser. No. 113,070, Feb. 5, 1971, Pat. No. 3,803,137, which is a continuation-in-part of Ser. No. 670,753, Sep. 26, 1967, abandoned.

[51] Int. Cl.[2] .............................................. C07C 85/06

[52] U.S. Cl. ........................ 260/585 B; 260/567.6 M; 252/88

[58] Field of Search .................................... 260/585 B

[56] References Cited

U.S. PATENT DOCUMENTS

| | | | |
|---|---|---|---|
| 2,953,601 | 9/1960 | Whitaker | 260/585 B |
| 3,223,734 | 12/1965 | Fallstad et al. | 260/585 B |
| 3,803,137 | 4/1974 | Egan et al. | 260/567.6 M |

FOREIGN PATENT DOCUMENTS

| | | | |
|---|---|---|---|
| 744,851 | 2/1956 | United Kingdom | 260/585 B |

OTHER PUBLICATIONS

Stevenson, Ind. & Eng. Chem., 40, (1948), pp. 1584–1585.

*Primary Examiner*—Joseph Paul Brust

[57] ABSTRACT

A mixture of specified long chain aliphatic alcohols is contacted at atmospheric pressure and at an elevated temperature with ammonia in the presence of a hydrogenation-dehydrogenation catalyst while continuously removing water of reaction and excess ammonia, to produce a mixture of aliphatic amines predominating in secondary amines. Such amine product is quaternized to yield corresponding mixtures of fabric softening quaternary ammonium compounds capable of providing aqueous dispersions thereof exhibiting outstanding stability characteristics at low concentrations of active content.

5 Claims, No Drawings

MIXTURES OF ALIPHATIC AMINES AND QUATERNARY AMMONIUM COMPOUNDS THEREOF

CROSS-REFERENCE TO A RELATED APPLICATION

This is a division of Ser. No. 113,070, filed Feb. 5, 1971, now U.S. Pat. No. 3,803,137, which in turn is a continuation-in-part of application Ser. No. 670,753, filed Sept. 26, 1967, now abandoned.

BACKGROUND OF THE INVENTION

1. Field of the Invention

This invention relates to mixtures of long chain aliphatic monoamines predominating in secondary amines, and to a process for the preparation thereof. In a further aspect, the present invention relates to aqueous dispersions of the quaternary ammonium compound mixtures derived from said long chain aliphatic amine mixtures.

2. Description of the Prior Art

Quaternary derivatives of long chain aliphatic secondary and tertiary mono-amines are known to possess fabric softening characteristics and hence these derivatives are currently used extensively in such an application. Since the quaternary derivatives of secondary mono-amines are more suitable softeners than the corresponding derivatives of the tertiary amines, the art has sought to develop a method for producing amines by ammonolysis of alcohols whereby secondary amines constitute a major to a predominant portion of the product mix. Hitherto, however, these methods have resulted in the production of amine products predominating in tertiary amines.

It is further known how to optimize the fabric softening characteristics of the quaternary compounds concerned by appropriate selection of the alcohol mixture to provide a suitable alkyl chain length distribution to the amine products from whence the quaternary compounds are derived. However, the aqueous alcoholic concentrates of these optimized compositions characteristically lack liquidity at room temperature and thus are difficult to disperse in preparing low active content dispersions thereof. Moreover, aqueous dispersions of the prior art compositions at the low active levels frequently used in house hold applications are prone to be unstable.

SUMMARY OF THE INVENTION

In accordance with this invention, mono-amine products are derived from a mixture of primary aliphatic alcohols having 8 to 22 carbon atoms per molecule, with at least 30 wt. % of said mixture, and preferably 40 to 70 wt. % of said mixture, being aliphatic primary alcohols having 16 to 20, and preferably 16 to 18 carbon atoms per molecule.

The foregoing mixtures are subjected to ammonolysis in a mixed phase at moderately elevated temperatures in the order of 180°–220° C. and atmospheric pressure by bubbling, sparging, or otherwise passing gaseous ammonia, preferably in admixture with gaseous hydrogen, through said alcohol mixture, in the presence of a hydrogenation-dehydrogenation catalyst dispersed therein. Ammonolysis is continued until the conversion of alcohol to amines is substantially complete, and the total amine nitrogen content of the resulting reaction product is substantially constant. The resulting mono-amine product predominates in the amount of secondary amines, e.g., 60 to 85 wt. %, and of the remainder, typically 0 to 10 wt. % will be primary amines and 5 to 25 wt. % will be tertiary amines.

In a further embodiment of this invention, an amine product is prepared from a mixture of straight-chain and branched alcohols which otherwise corresponds to the molecular weight distribution noted above, whereupon said amine product is quaternized to provide a mixture of quaternary ammonium compounds. Due to the relationship of straight-chain to branched alcohols comprising the mixture utilized in making the amine product contemplated in this embodiment and the conditions of ammonolysis described above, the resultant quaternized product is not only a highly effective fabric softener but additionally possesses a variety of outstanding physical properties. The latter can be summarized as follows:

(1) Liquidity at room temperature exhibited by the aqueous alcoholic concentrates thereof (2) Ease with which aqueous dispersions can be prepared from such concentrates (3) Outstanding stability characteristics exhibited by the aqueous dispersions thereof having a low active content (4) Stability of the aqueous dispersions toward freeze-thaw cycling

DESCRIPTION OF THE PREFERRED EMBODIMENTS

As indicated hereinbefore, the nature or makeup of the starting or charged alcohol mixture is, in itself, of critical importance in obtaining an amine product whose quaternized derivative exhibits the improved water-dispersibility and other properties noted therefor. In addition to the molecular weight distribution specified above for the composite primary alcohols, it is essential for the purpose of achieving the indicated improvements that the component alcohols of said mixtures having 16 or more carbon atoms be straight-chain alcohols and that those having less than 16 carbon atoms contain a substantial amount of species having predominately single methyl branching. In context of the foregoing, the alcohol mixtures broadly applicable contain overall from about 95 to 80 wt. % of straight-chain alcohols and correspondingly from 5 to 20% of said branched alcohols. More preferably, such mixtures are composed of from about 90–85 wt. % straight-chain alcohols and correspondingly from 10–15% of the branched alcohols.

The alcohols useful in the practice of this invention are commonly called fatty alcohols. They have long been commercially available from natural fatty esters and more recently from synthetic or petroleum sources, either as substantially single component alcohol product or as mixtures of alcohols. The alcohols can be saturated or ethylenically unsaturated. However, saturated alcohols are preferred since unsaturated alcohols will result in quaternized products having a tendency to cause yellowing or discoloration of the treated fabric.

For economic reasons, the commercially available synthetically derived straight-chain primary alcohols are preferred. The latter alcohols are obtained by polymerizing ethylene in accordance with Ziegler chemistry. The branched primary alcohols useful herein likewise are commercially available as mixtures with the straight-chain isomers. Such mixtures containing branched isomers, i.e., predominately single methyl branching, are readily obtained in the production of long chain alcohols by the OXO process. Normally the alcohols produced in this manner will contain from 20–30% of said branched isomers. Accordingly, one can employ mixtures of the OXO alcohols and the Ziegler alcohols in order to obtain starting alcohol mixtures having a content of branched isomers noted above for use in preparing the mono-amine products suitable for deriving the quaternary compounds contemplated herein.

As indicated hereinabove, any hydrogenation-dehydrogenation catalyst previously used in the prior art in the ammonolysis of alcohols can be used in preparing mono-amine products in accordance with this invention. It has been noted, however, that supported nickel catalysts, especially nickel supported on Keiselguhr, are preferred for highest yields of secondary amines. An applicable catalyst of this type is disclosed in U.S. Pat. No. 3,264,354. Generally, the amount of catalyst is from about 0.5–10 wt. % and preferably 1–4 wt. % based on the weight of the charged alcohol mixture.

In carrying out the ammonolysis reaction, the alcohol mixture is charged to a suitable reactor and moderately heated; whereupon the catalyst is charged and dispersed in the liquid alcohol with agitation. Gaseous ammonia is then continuously bubbled up or sparged through the liquid alcohol, preferably along with hydrogen, while sufficient heat is used to sustain the desired reaction at atmospheric pressure. The water of reaction and unreacted or by-product ammonia are continuously removed from the reactor.

An applicable reaction temperature range for effecting the ammonolysis reaction is from about 180°–220° C. and more preferably from 185°–195° C. The amount of gaseous ammonia is from about 2.2 to 6 wt. % per hour, preferably 3–5 wt. %, based on the weight of the charged alcohol mixture. Hydrogen, where used (and such use is preferred in order to maximize conversion of alcohol to amine), will amount from up to 50 vol. %, or higher, e.g., 100 vol. % and preferably 25–75 vol. % of the vol. flow rate of the ammonia.

Initially, the reaction mixture is desirably sparged with ammonia and hydrogen at 25–75% of their normal rates until the temperature reaches the indicated reaction range and then at their full rates. The reaction is continued in this manner until the total amine nitrogen content (TAN) is substantially constant and conversion of the alcohol to amine is substantially complete. Generally, the total amine nitrogen will rise to about 2.5 to 4, preferably 2.8 to 3.1 and will be considered constant if it remains at a value in this range ±0.1, during an hour's time. The conversion of the alcohol to amine at the point where constant TAN is obtained will be substantially complete, e.g., at least 75% and preferably 85% or higher, and at this point the amount of secondary amine in the product will predominate. If it is desired to increase the amount of tertiary amine in the product, the reaction mixture can be continued to be heated at said reaction temperatures beyond the time constant TAN is reached until the higher tertiary amine content is obtained (the amount of secondary amine, however, still will be predominant, i.e., 65% or more).

As mentioned above, the amine product produced by the aforedescribed ammonolysis procedure is especially useful as an intermediate in the preparation of a fabric softening quaternary ammonium compound mixture. The quaternizing agent used to quaternize the amine product can suitably be a lower alkyl halide having 1 to 3 carbon atoms, such as methyl chloride (the preferred quaternizing agent), ethyl chloride, isopropyl chloride, propyl chloride, and the like, as well as the corresponding bromides and iodides. The quaternized product will be a mixture of the following quaternary ammonium compounds:

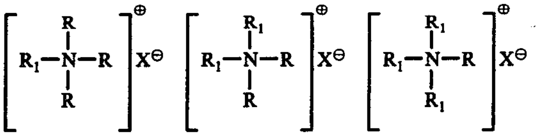

I II III wherein $R_1$, from a carbon atom content standpoint, represents an aliphatic group having 8 to 22 carbon atoms, at least 30% of the $R_1$'s present in the mixture having 16–20 carbon atoms, R is a lower alkyl having 1 to 3 carbon atoms, and X is a halide anion. Preferably, $R_1$ is an alkyl group having 12 to 18 carbon atoms, at least 40 to 70% of the $R_1$'s present in the mixture having 16 and/or 18 carbon atoms, R is methyl, and X is a chlorine anion. The $R_1$ substituents likewise comprise a mixture of straight-chain and single methyl branched groups providing the relationship of such groups as noted hereinabove. Generally, said mixture will comprise 0–10 wt. % of compounds of Formula I, 60–85 wt. % of compounds of Formula II, and 5–25 wt. % of compounds of Formula III. Typically, for use of said mixture in fabric softeners, the mixture will comprise 0–5 wt. % of compounds of Formula I, 75–80 wt. % of compounds of Formula II, and 10–20 wt. % of compounds of Formula III.

It is also within the scope of this invention to quaternize the amine mixture with other conventional quaternizing agents, including the mineral acids, such as hydrochloric acid and sulfuric acid, and organic acids, such as acetic acid, chloroacetic acid, benzoic acid, benzene sulfonic acid, and toluene sulfonic acid, and esters of such acids, for example, methyl chloroacetate, vinyl chloroacetate, dimethyl sulfate, benzyl chloride, methylbenzyl chloride, chlorobenzyl chloride, nitrobenzyl chloride, methyl and ethyl esters of benzene sulfonic acid and toluene sulfonic acid, and other known quaternizing agents, such as disclosed in U.S. Pat. No. 3,141,905.

The quaternization of the amine product is preferably accomplished by introducing the quaternizing agent (e.g., methyl chloride) into a closed vessel containing the amine product and alkali (e.g., caustic, sodium or potassium carbonates, bicarbonates, and hydroxides) and carrying out the reaction at elevated temperature (e.g., 90°–100° C) and under pressure (e.g., 40–50 psig). The alkali can be used in the form of an aqueous slurry, sufficient alkali being used to neutralize any amine hydrohalide and hydrohalide. The reaction is also preferably carried out in a low molecular weight, water misicible alkanol or a glycol, such as methanol, ethanol, or isopropanol (the preferred solvent), ethylene glycol, diethylene glycol, mono lower alkyl ethers of ethylene glycol, and the like. These water-miscible solvents will aid the rate of quaternization and further facilitate the dispersibility of the quaternized product in water and/or the fluidity and subsequent handling of the product. The amount of solvent used can vary and generally will be 5 to 50 wt. % preferably 10 to 25 wt. %, of the reaction mixture. During the course of quaternization, samples can be withdrawn and analyzed for free amine and amine hydrohalide, and further quaternizing agent introduced until the former is nil and further alkali introduced until the latter is nil. Following quaternization, the reactor can be cooled and vented and product vacuum stripped to remove excess or residual quaternizing agent, and the product then filtered to remove the sodium chloride formed during the reaction. If desirable, the wt. % of the dissolved solids in the product can be adjusted with water or alcohol.

In the preferred quaternization, where the amine product is to be quaternized with methyl chloride, the amine product is first mixed with a sufficient amount of about 80 wt. % aqueous isopropanol so that the resulting quaternized product will contain about 75 wt. % solids. Such concentrates will be a clear, stable, uniform liquid dispersion having a pour point as low as 25°-35° F (without requiring use of pour point depressants) and will be dispersible in cold (e.g., as low as 32° F) water (without requiring use of dispersing aids, or high shear or vigorous agitation). The resultant product can be sold as such to fabric softener formulators or packagers and diluted with water to any concentration for sale to the ultimate user. Commercial launderers generally require a 25-50 wt. % solids dispersion, and the housewife generally uses 2-8 wt. % solids dispersion; either of these types of dispersions can easily be prepared from the concentrate by simply diluting the same with water without requiring the heating and high shear or vigorous agitation necessary in diluting prior art fabric softener concentrates. Both the concentrate and diluted formulations have excellent freeze-thaw stability without requiring the use of freeze-thaw stabilizers. The ability of the concentrate to be diluted in this fashion is very important from a commerical standpoint.

In evaluating the softening property, 8 pounds of desized bath towels are washed in a top-loading automatic washing machine using a commerical heavy duty detergent composition at the manufacturer's recommended concentration. Sufficient fabric softener is added to the final rinse cycle to give about 0.1 wt. % active softener, based on the weight of the towels. The washed towels are dried in an automatic drier and stored for 24 hours at 70° F and 50% relative humidity. The hand of the towels are then rated according to a scale of 1 to 5; a rating of 1 is the softest and a rating of 5 is the harshest, with a rating of 5 being assigned to the control towel (i.e., one washed or rinsed in the absence of softener). In evaluating the softening property of the disclosed composition in accordance with this procedure, ratings of about 1.5 to 2.5 have been obtained, attesting to the excellence of the product as a fabric softener.

Another evaluation test performed is the so-called "drop-glisten" test. In this test, a drop of water is placed on a towel softened as described in the preceding paragraph, and the time of absorption of the drop (i.e., how long it takes for the glisten of the drop to disappear) is measured. In so evaluating towels softened with the quaternary ammonium chloride compounds having the disclosed above, the time of absorption (i.e., the rewetting time) has been found to be about 12 to 25 seconds, which is significantly superior to rewetting times of prior art softeners such as di(hydrogenated tallow) dimethyl ammonium chlorides which commonly exhibit a rewetting time of about 30-33 seconds and is significant when compared to untreated or control towels which have rewetting times of about 7 seconds.

In addition, fabric softeners made from said 75 wt. % concentrate, as well as the concentrate itself, has excellent freeze-thaw stability, and such fabric softener also will impart anti-static properties of fabrics treated therewith, as well as lubricity, and will make fabrics easier to iron. If desired, dyes, optical brighteners, and perfumes can be added to increase the attractiveness or appeal of the concentrate or diluted product. Also, germicidal sanitizing agents, can be incorporated in the fabric softener formulation, particularly in 75% concentrates. It should be also understood that the concentrate or diluted product can be used in textile operations as a textile lubricant or finishing aid, as well as being used in commerical or home laundry operations. Fabrics or fibers so-treated will have improved drapeability, wrinkle recovery, and the softened fabrics will also dry faster since they will retain less moisture after spin-drying.

The following example illustrates the best mode contemplated for carrying out the present invention. However, it should be understood that the various materials and amounts thereof used in this example, as well as conditions of reaction are not to be construed to unduly limit this invention.

EXAMPLE I

A reactor is charged with an equi-weight mixture of Neodol 25 (Shell Chemical Co.) and Alfol 1618 (Continental Oil Co.). The latter is a mixture essentially composed of n-hexadecanol-1 and n-octadecanol-1. The Neodol 25 alcohol mixture is essentially composed of $C_{12}$-$C_{15}$ primary alcohols containing from about 20 to 25% of predominantly single methyl branched isomers with the balance being straight-chain isomers. A typical isomeric makeup of an equi-weight mixture of said alcohol products is tabulated below where sc denotes the straight-chain isomers and b denotes the branched isomers.

| | |
|---|---|
| $C_{11}$ | 1.0 |
| $C_{12\,sc}$ | 9.25 |
| $C_{12\,b}$ | 3.10 |
| $C_{13\,sc}$ | 9.40 |
| $C_{13\,b}$ | 3.15 |
| $C_{14\,sc}$ | 11.65 |
| $C_{14\,b}$ | 3.55 |
| $C_{15\,sc}$ | 7.35 |
| $C_{15\,b}$ | 2.40 |
| $C_{16\,sc}$ | 31.50 |
| $C_{18\,sc}$ | 17.00 |
| $C_{20}$ | 0.50 |

The mixture of alcohols is then heated to 200°-220° F. with agitation to melt normally solid alcohol components in the mixture. Catalyst (Girdler-G49B) is then charged in an amount equal to 1.75 wt. % of the alcohol mixture. Gaseous ammonia and hydrogen are then continuously sparged through the reaction mixture, the ammonia, at a rate of about 2 wt. % per hour, based on the weight of the alcohol mixture, and the hydrogen at a rate equal to about 12.5 vol. % of the ammonia rate, and heating continued. When the temperature of the reaction mixture reaches about 372° F., the ammonia and hydrogen sparge rates are doubled and a sample withdrawn for analysis of the total amine nitrogen content of the reaction mixture. Samples are periodically withdrawn thereafter in one hour intervals during the course of reaction, while maintaining the temperature of the reaction at 370°-375° F. TAN analyses of one run are shown in Table I.

TABLE I

| Time of Reaction* | 0 | 1 | 2 | 3 | 4 | 5 | 6 |
|---|---|---|---|---|---|---|---|
| TAN | 0.84 | 1.89 | 2.52 | — | 3.06 | 3.19 | 3.18 |

*Hours after reaction mixture initially reached reaction temperature, 372° F.

During the course of reaction, water and ammonia by-products are continuously removed from the reactor. When TAN is found to be substantially constant, the ammonia and hydrogen sparges are stopped and the reaction mixture cooled to 220°-230° F. The reactor is then sealed and 12--15 inches of mercury vacuum applied to remove residual ammonia and hydrogen from the reaction mixture and thereupon the resulting amine product is filtered. The product had the following analysis:

TABLE II

| | |
|---|---|
| Total amine nitrogen | 3.18 |
| Primary amine, wt. % | 3.7 |
| Secondary amine, wt. % | 76.7 |
| Tertiary amine, wt. % | 16.9 |

The above-described amine product is then quaternized by charging it to a reactor together with 73% caustic (sodium hydroxide) and isopropanol alcohol. The reactor is then heated to 190°-200° F. and sealed, and gaseous methyl chloride is pumped into the agitating reaction mixture to maintain the reactor pressure at 40-45 psig. The quaternization is continued while periodically samples are withdrawn for analysis of free amine and amine hydrohalide. Methyl chloride is continuously fed into the reactor until the free amine content is less than 1.5 wt. %, and further caustic added as necessary until the amine hydrohalide is reduced to less than 0.5 wt. %. When these conditions are reached, the methyl chloride supply is stopped and the reactor cooled to about 130° F. and vented to atmospheric pressure to remove residual methyl chloride. Further isopropanol is added to the resulting quaternized product as necessary to adjust the dissolved solids content to 75 wt. %. The adjusted product is then filtered to remove by-product sodium chloride. The final quaternary ammonium chloride product had the following analysis:

TABLE III

| | |
|---|---|
| Quaternary ammonium compounds | 69.3 wt. % |
| Unreacted alcohol and by-products | 5.7 wt. % |
| Isopropanol | 19.2 wt. % |
| Water | 5.8 wt. % |

The above-described quaternary ammonium chloride product (75 wt. % solids) is a stable, uniform clear liquid having a pour point of 35° F. and a freezing point of 28° F. with a Gardner color of $1^-$ and an ash (NaCl) content of 0.01 wt. %. It can be dispersed in cold water (as low as 32° F.) without requiring high sheer or vigorous agitation to form dilute aqueous liquid dispersions active quaternary ammonium chloride contents as low as 6 wt. % or lower. When evaluated as a fabric softener by the aforedescribed softening test, it resulted in a rating of 1.8 and when evaluated by the aforedescribed drop-glisten test it has a rewetting time of 22 seconds, values which, especially when considered with the above-described physical properties, show the quaternized product of this invention has excellent utility in fabric softening.

Although the quaternized product of this invention finds particular utility in fabric softening compositions, the broadest aspects of this invention should not be limited thereto, since the quaternized product can also be used in rinsing composition for human hair, as an emulsifier of oil and water emulsions, and as an antistatic agent for paper, fabric, polishes, etc.

What is claimed is:

1. A process for the conversion of a $C_8$–$C_{22}$ primary aliphatic hydrocarbon mono-alcohol to a $C_8$–$C_{22}$ monoamine containing from 60–85 wt. % secondary amine derivatives which comprises sparging said alcohol at a temperature of from 180°-220° C. in the presence of from 0.5–10 wt. % nickel hydrogenation-dehydrogenation catalyst with a gaseous mixture of ammonia and hydrogen having a volumetric ratio of 8:1 to 1:1, respectively, at a rate of from 2.2–6 wt. % ammonia per hour based on the weight of the alcohol and continuously removing water of reaction and excess ammonia, and wherein the ammonolysis reaction is carried out until the total amine nitrogen content of the reaction mixture remains substantially constant.

2. A process in accordance with claim 1 wherein the ammonia is introduced into said alcohols at a rate of 3–5 wt. % per hour based on the weight of the alcohol mixture.

3. A process in accordance with claim 2 wherein said catalyst is a supported nickel catalyst present in an amount of from about 1–4 wt. % of said alcohol mixture.

4. A process in accordance with claim 3 wherein the reaction temperature is from about 185° to 195° C.

5. A process in accordance with claim 4 wherein the hydrogen is introduced into said alcohols at a rate of about 25–75 vol. % based on the rate of said ammonia.

* * * * *